United States Patent [19]
Trew et al.

[11] Patent Number: 5,561,718
[45] Date of Patent: Oct. 1, 1996

[54] CLASSIFYING FACES

[75] Inventors: Timothy I. P. Trew; Richard D. Gallery, both of Horley, England

[73] Assignee: U.S. Philips Corporation, New York, N.Y.

[21] Appl. No.: 328,980

[22] Filed: Oct. 24, 1994

Related U.S. Application Data

[63] Continuation of Ser. No. 4,861, Jan. 18, 1993, abandoned.

[30] Foreign Application Priority Data

Jan. 17, 1992 [GB] United Kingdom .................. 9201006

[51] Int. Cl.$^6$ .................................................. G06K 9/00
[52] U.S. Cl. .......................... 382/118; 382/203; 382/224; 382/276
[58] Field of Search ................................... 382/2, 10, 14, 382/37, 42, 43, 16, 19, 118, 117, 115, 159, 160, 181, 190, 195, 203, 224, 226, 276, 278, 280

[56] References Cited

U.S. PATENT DOCUMENTS

| | | | |
|---|---|---|---|
| 4,084,255 | 4/1978 | Carasent et al. | 364/822 |
| 4,975,969 | 12/1990 | Tal | 382/116 |
| 5,161,204 | 11/1992 | Hutcheson et al. | 382/16 |
| 5,164,992 | 11/1992 | Turk et al. | 382/2 |

FOREIGN PATENT DOCUMENTS

| | | | |
|---|---|---|---|
| 2231699 | 11/1990 | United Kingdom | 382/2 |

OTHER PUBLICATIONS

"Experiments on Pattern Recognition Using Invariant Fourier–Mellin Descriptors" Sheng et al, Journal of the Optical Society of America vol. 3, no. 6, Jun. 1986, pp. 771–776.

"A Transformation Invariant Recursive Subdivision Method for Shape Analysis" Zhu et al, IEEE Proceedings of the 9th International Conference on Pattern Recognition, vol. 2, Nov. 17, 1988 pp. 833–835.

"A New Filter Structure for the Implementation of Certain Classes of Image Processing Operations" Pitas et al, IEEE Transactions on Circuits and Systems vol. 35, no. 6, Jun. 1988, pp. 636–647.

"Finding Face Features" Craw et al, Proceedings of the Second European Conference on Computer Vision, ECCV'92 May 23, 1992, pp. 92–96.

L. Sirovich and M. Kirby, "Low–dimensional procedure for the characterization of human faces", Optical Society of America, vol. 4, pp. 519–524, Mar. 1987.

*Primary Examiner*—Leo Boudreau
*Assistant Examiner*—Phuoc Tran
*Attorney, Agent, or Firm*—Leroy Eason

[57] ABSTRACT

A face classification system which receives video data representative of a scene and extracts therefrom data representative of a face which is present in the scene. The facial video data is applied to a homomorphic filter to eliminate the effects of lighting changes in the scene. The positions of the eyes and mouth are located to form two sub-divisions, one in relation to a first line joining the eyes and the other in relation to a second line perpendicular to the first line and passing through the nose. A feature vector which is representative of the face and is rotation, scaling, translation and grey level intensity invariant is then produced by applying a recursive second order sub-division of moments to the filtered data. Such sub-division of moments is constrained to act first on the sub-divisions formed by the aforesaid lines, thereby reducing the effect of noise. The feature vector may be applied to a classifier which employs multi-layer perception to compare it with stored feature vectors of faces in one or more previous scenes to determine if the faces match. The system may be used, for example, for allowing access to secure areas or to secure computer work stations.

5 Claims, 3 Drawing Sheets

CLASSIFYING FACES

This is a continuation division of application Ser. No. 08/004,861, filed Jan. 18, 1993, now abandoned

BACKGROUND OF THE INVENTION

The invention relates to a face classification system. The invention further relates to a security system capable of identifying persons using face classification.

Any method of face classification divides naturally into two stages; a) Face location and b) Classification.

A survey of the use of face recognition for security applications by M. Nixon, "Automated Facial Recognition and its Potential for Security" IEE Coloquium on "MMI in Computer Security", (Digest No. 80) (1986), classifies face recognition techniques as either statistical or structural in side view or front view. For front view the structural techniques are further classified in terms of feature measurements and angular measurements.

Any system which is to operate in an unconstrained environment, must use a structural approach which incorporates some knowledge of the structure of a face so that features may still be located under varying lighting conditions, background and pose. Metrics are constructed based upon the relationships between located facial features, and are then used to classify the face. One problem with this approach is choosing appropriate metrics. For example, R. Buhr, "Front Face Analysis and Classification (Analyse und Klassification von Geischtsbildern)", ntz Archiv 8, No. 10, pp 245–256 (1986) proposed using 45 measures. Additionally, for such an approach it is necessary to locate the facial features with high precision. Other examples of this approach are exemplified by R. J. Baron, "Mechanism of Human Facial Recognition", Int. J. Man-Machine Studies, 15, pp 137–178 (1981) and T. Sakai, M. Nagao & M. Kanade, "Computer Analysis and Classification of Photographs of Human Faces", Proc. 1st USA-Japan Computer Conf. AFIPS Press, New Jersey, pp 55–62 (1972).

The attraction of the statistical approach is the possibility that simple methods may be employed to extract feature vectors. I. Aleksander, W. V. Thomas & P. A. Bowden have disclosed in "A Step Forward in Image Recognition", Sensor Review, July, pp120–124 (1984) a statistical face recognition system, using WISARD, which is able to recognize a pattern within one frame period. The main shortcoming of this system is that it is specific to a particular position and orientation, so the individual's characteristics must be learnt for a series of spatial displacements, reducing the reliability of the identification and reducing the storage capacity of the system.

A departure from the either wholly statistical or wholly structural approaches is disclosed by I. Craw & P. Cameron, "Parameterising Images for Recognition and Reconstruction", BMVC 91, pp 367–370, Springer-Verlag (1991) which uses a hybrid structural/statistical approach, in which a large number of feature points are utilized to normalize the shape of the face, and then principal component analysis is used to obtain a lower dimensional representation of the face. This is compared with a database of similarly encoded faces for recognition purposes. Such a hybrid approach offers the advantage of not having to constrain the face unduly (structural), and also retains the significant advantages of statistical methods.

SUMMARY OF THE INVENTION

The invention provides a face classification system comprising first means for locating a two dimensional representation of a scene, second means for locating the face in the representation of the scene, third means for forming a rotation, scaling, translation and grey level intensity invariant representation of the face and producing a feature vector therefrom, and fourth means for comparing the feature vector of the presently located face with the stored feature vector of a previously located face to determine whether the presently located face matches the previously located face.

By forming a rotation, scaling, translation, and grey level intensity invariant representation of the face constraints on the position and orientation of the face and on the scene lighting can be relaxed, enabling the face classification to be carried out unobtrusively as far as the person being classified is concerned.

A homomorphic filter may be provided for producing a grey level intensity invariant representation.

This is a convenient way of minimizing the effects of lighting changes in the scene.

The third means may comprise means for fitting an outline to the face and means for performing a recursive second order subdivision of moments on the outlined face.

This produces a short feature vector which enables minimization of the storage required for the representation of a face and also has the advantage of using information from the whole face and not just the boundary or other edges.

The face classification system may further comprise means for locating the eyes and nose on the face, means for subdividing the face by two lines, one joining the eyes and the other perpendicular thereto and through the nose, and means for performing the recursive second order subdivision of moments on the sub-divided areas of the face, the first sub-division taking place on the line joining the eyes and the second sub-division taking place on the perpendicular line.

The recursive second order sub-division of moments is purely statistical in its operation and is noise sensitive in that a small perturbation in the location of the center of gravity will change the subsequent subdivisions substantially. By including structural information, that is by constraining the initial sub-division to take place through the eyes such that two regions are formed and then perpendicular to the previous subdivision through the nose so that each region is further divided in two, the transformation is made more robust and less sensitive to noise.

The third means may alternatively comprise means for fitting an outline to the face, means for locating the midpoint between the eyes, and means for performing a Fourier-Mellin transformation on the face referenced to the midpoint between the eyes to produce a feature vector of the face.

The Fourier-Mellin transformation is relatively insensitive to noise but on a global picture is not translation invariant. By locating the mid-point between the eyes and referencing the transformation to that point an effectively translation invariant transformation can be obtained.

The invention further provides a security system comprising a video camera, means for locating a face within a picture frame produced by the video camera, means for forming a rotation, scaling, translation and grey level intensity invariant representation of the face and producing a feature vector therefrom, means for storing a corresponding feature vector for at least one previously located face, means for comparing the feature vector of the presently located face with the feature vector of the at least one previously located face to determine whether the present face matches the at least one previously located face, and means for initiating a security measure if the two faces are not matched.

There are many potential areas of application for security systems including an automatic face identification system. Automatic access to secure areas is one example, in which the face of the individual seeking to enter might be compared with a data base of faces of individuals allowed access, optionally with additional verification by personal identification number. Another potential area of application is in preventing credit card fraud. This might involve the encoding of a feature vector, representing the face of the individual authorised to use the card onto the card's memory, which could then be compared with the face of the individual attempting to use the card during transactions. Of critical importance in this application is the length of the feature vector, which must fit within the memory supported by the card. Thus in such an application, the facial feature extraction method used must also compress the facial data presented to it. Use of the recursive second order sub-division of moments is one way of fulfilling this requirement.

It is also important to minimize the amount of space the stored feature vectors occupy in central memory for the automatic access to secure areas if the data base of authorized persons is extensive. While it would be possible where access to a secure area is concerned to compare the face presented at the entrance with all authorised persons stored in the data base it may be preferable to have a personal identification number allocated to each authorised person and to use this number to identify the stored feature vector of the face of the person seeking entry for comparison with that produced by an entry camera.

An alternative procedure with credit cards would be to have a central data base of feature vectors of all card holders and for the transaction terminal to view and form a feature vector of the card user. This feature vector would then be transmitted to the central data base where the comparison would be made, optionally using credit card data to address the appropriate feature vector in the data base. Subsequently an authorization signal would be relayed to the transaction terminal. This removes the need to store the feature vector on the card and hence removes the constraint on the length of the feature vector caused by the storage capacity of the card. It is still, however, desirable to minimise the length of the feature vector to reduce the required capacity of the central data base and also the transmission time required for transmission of the feature vector from the transaction terminal to the central data base.

By transmitting the feature vector to a central data base the complexity of the transaction terminal can be minimized in that the comparison means for the feature vectors is not required to be present in the transaction terminal. There will, of course, be many transaction terminals connected to the card verification data base and minimizing their cost is important in the provision of a comprehensive system.

Such a security system for use with a computer terminal may comprise means for locating the user's face at logon, means for forming a rotation, scaling, translation, and grey level intensity invariant representation of the face and producing a feature vector therefrom, means for storing the feature vector, means for periodically locating the user's face and forming a rotation, scaling, translation, and grey level intensity invariant representation thereof and producing a feature vector therefrom, and means for comparing the feature vector of the presently located face with the feature vector of the face at logon.

As the use of workstations in financial, and other commercial environments, becomes more widespread, workstation security is becoming of paramount importance. A major problem in maintaining the integrity of workstation security is that of, authorised users leaving a terminal unattended without logging out or putting it into pause mode. Unauthorized users may then gain access to the system. One existing solution to this problem is password verification, either periodically, or if the keyboard is unused for some time, which is of course a relatively obtrusive method. Another, biometric, technique used is based upon the analysis of the keystroke rhythm of the authorized user. However such techniques encounter difficulty in coping with individuals whose typing style changes when performing different tasks.

By continuously monitoring the facial features of the user it is possible to ensure that no one else has taken over use of the terminal since logon.

BRIEF DESCRIPTION OF THE DRAWINGS

The above and other features and advantages of the invention will be apparent from the illustrative embodiments of the invention which will now be described with reference to the accompanying drawings, in which.

DETAILED DESCRIPTION OF THE PREFERRED EMBODIMENT

Figure 1:
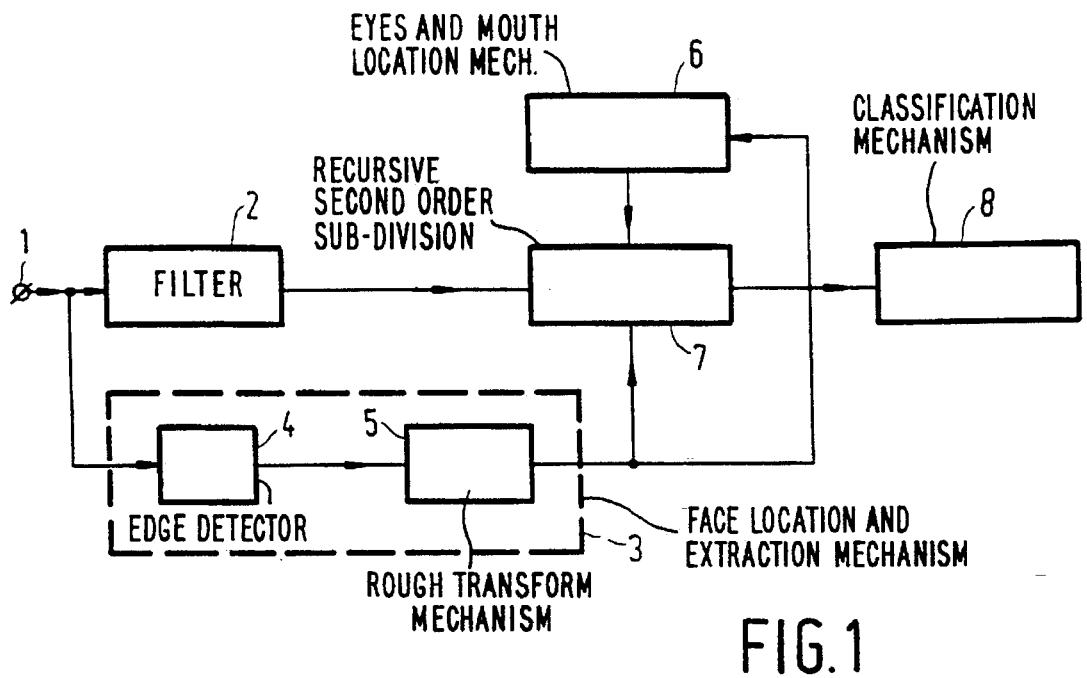
FIG. 1 shows in block schematic form one embodiment of a face classification system according to the invention.

As shown in FIG. 1 image data from a video camera (not shown) is applied via an input 1 to a homomorphic filter 2 to remove the effects of lighting changes on the representation of the scene. The image data is also fed to a face location and extraction unit 3. In this particular embodiment the face location and extraction unit 3 comprises an edge detector 4 and Hough transform unit 5 but it could take other forms, for example that disclosed by E. Badiqué in a paper entitled "Knowledge-Based Facial Area Recognition and Improved Coding in a CCITT-Compatible Low-bitrate Video-Codec" presented at the Picture Coding Symposium at Cambridge, Mass. 26–28th March 1990.

A simple model of the outline of a face is an ellipse, and an architecture for fitting ellipses to faces is disclosed by S. A. Rajala and A. M. Alattair in "A Parallel/Pipeline Structure for the Primitive-Based Image Codec for Coding Head and Shoulders Images" PCS90, pp 9.16–9.17 (1990). More accurate modelling of faces in which simulated annealing is used to fit a head outline to a face is described by A. Bennet and I. Craw in "Finding Image Features Using Deformable Templates and Detailed Prior Statistical Knowledge". BMVC 91, pp 233–239, Springer-Verlap (1991).

The location of the eyes and mouth within the face is determined by eyes and mouth location mechanism 6. This may be achieved from a knowledge of the geometry of the face and from detecting areas of highest movement. Thus the eyes and mouth are frequently changing in shape and are at the corners of a triangle.

A transform unit 7 then applies a recursive second order sub-division of moments to the filtered image data from the homomorphic filter 2. This transform is restricted to the face region using the model of the outline of the face produced by the face extraction and location unit 3 and is constrained by, first, a sub-division on a line joining the two eyes, and second, a sub-division on a line perpendicular thereto passing through the nose. By constraining the sub-divisions the effects of noise can be reduced. The recursive second order sub-division of moments produces a feature vector characteristic of a given face. This is fed to a classification unit 8 which compares the feature vector just obtained with a stored feature vector to determine whether it represents the same face. The classification unit 8 may be a multi-layer perception which can be trained in known manner to classify the faces. For suitable training methods reference could be made to the textbook "Neural Computing—Theory and Practice" by Philips D. Wasserman published by Van Nostrand Reinhold, New York.

Figure 3:
FIG. 3 illustrates the feature vectors produced by the second order moment sub-division faces.
Figure 3:
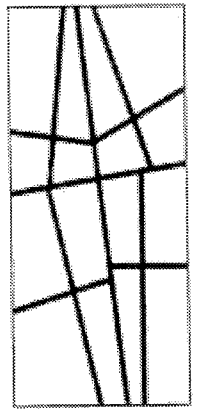
Figure 3:
Figure 3:
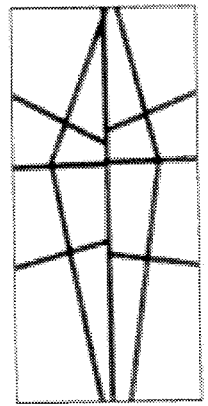
Figure 3:
Figure 3:
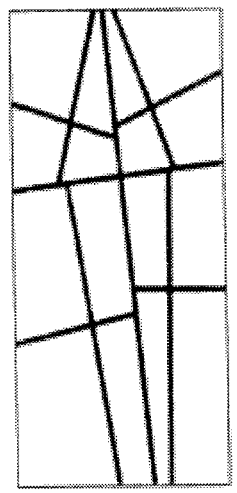
Figure 3:
Figure 3:
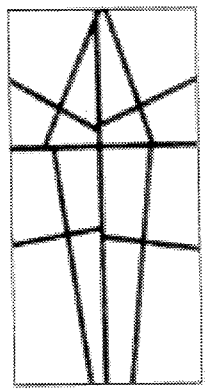

FIG. 3 shows examples of the feature vectors produced by the second order sub-division of moments constrained by a first sub-division on a line joining the eyes and a second sub-division on a line perpendicular thereto through the nose for two instances of the faces of two individuals.

Figure 2:
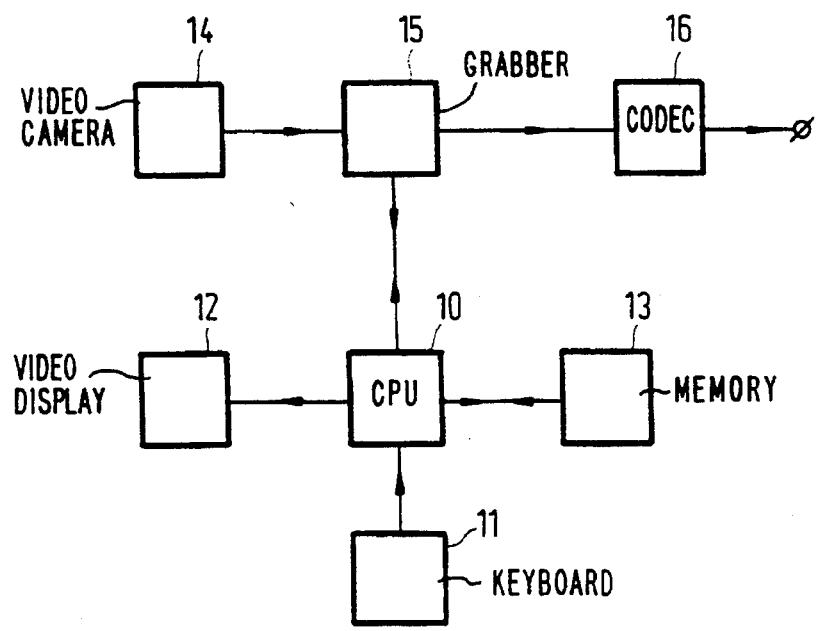
FIG. 2 shows in block schematic form one embodiment of a computer workstation in which a face classification system according to the invention is incorporated.

FIG. 2 shows in block schematic form a computer workstation which comprises a central processing unit 10 having connected to it, a keyboard 11, a video display unit (VDU) 12, and a memory 13. A video camera 14 is mounted to view a user of the computer workstation and provides an output which is fed to a frame grabber 15 and Codec 16. The output of the frame grabber 15 is also fed to the central processing unit 10.

Figure 4:
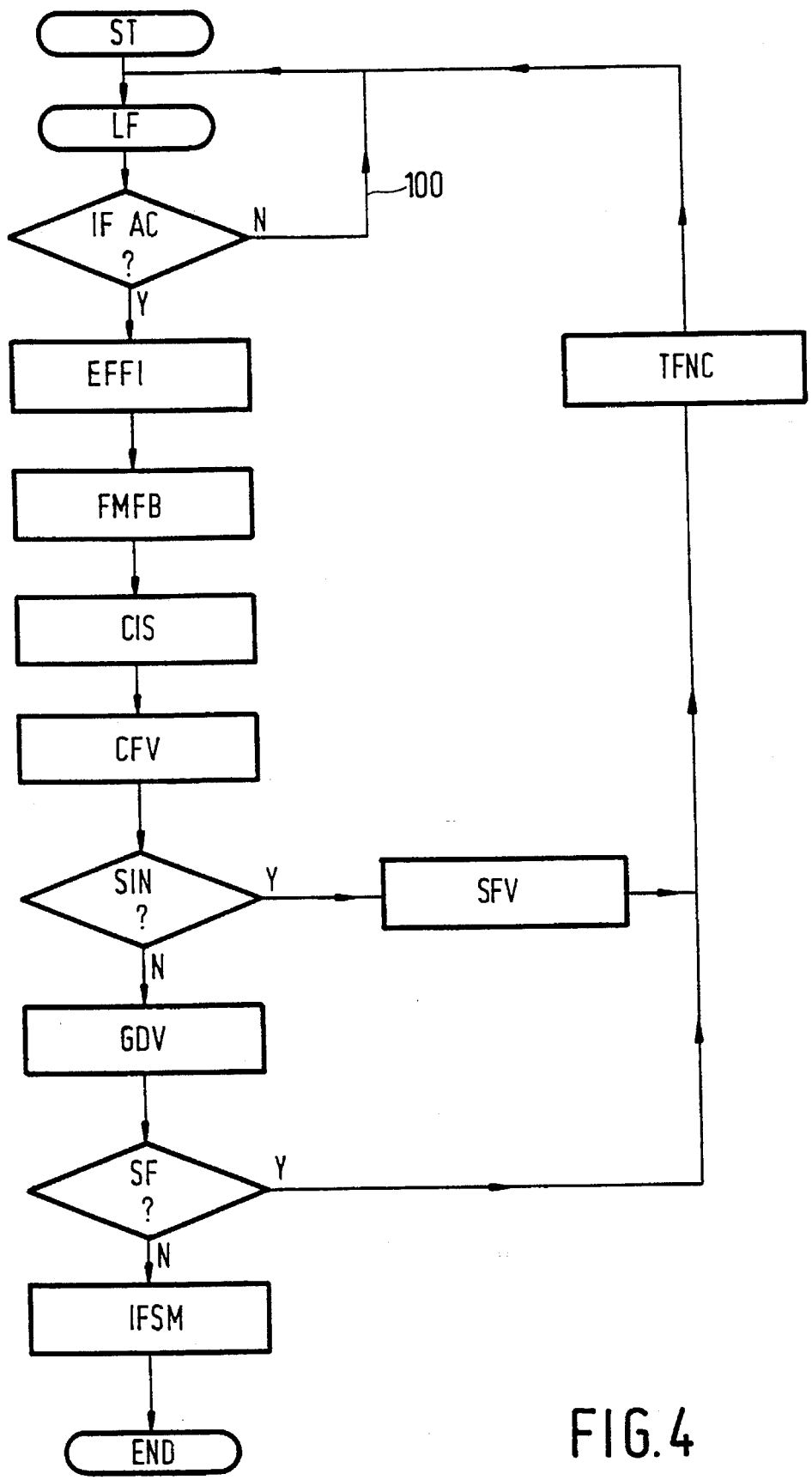
FIG. 4 is a flow diagram illustrating the operation of a security system for a computer workstation.

The flow diagram shown in FIG. 4 illustrates the operation of the security system incorporated in the workstation shown in FIG. 3. At the commencement ST (start), i.e. logon of the operator, the video camera frames are grabbed by the frame grabber 15 and the central processing unit 10 performs the homomorphic filtering of the image data and the face location as illustrated by box LF (locate face). A decision is then taken IFAC? (is face aligned correctly?) as to whether the face is correctly aligned, for example whether both eyes are visible to the camera. If the camera is mounted adjacent to the VDU this will usually be the case but if the decision is N (no) then loop 100 is followed and further frames are grabbed until the face is correctly aligned. Once a correctly aligned face has been detected it is extracted from the image EFFI (extract face from image) and then a model, for example an ellipse, is fitted to its boundary FMFB (fit model to facial boundary). The calculation of the recursive second order sub-division of moments is then commenced constrained by the initial sub-division through the eyes CIS (constrain initial sub-division) and the feature vectors calculated CFV (calculate feature vector). A decision is then made as to whether this is the system initialization run SIN? (is this the system initialisation run?) and if Y (yes) then the feature vector is stored SFV (store feature vector) for comparison with feature vectors calculated on later images. There is then a pause for a predetermined time WFNC (wait for next check) until the next check is to be done when the face location check LF is made.

If it is not the system initialization run then the feature vector obtained is compared with the stored feature vector and a difference vector is generated GDV (generate difference vector). A decision is then made as to whether the same face has been located by thresholding the difference vectors SF? (same face?) Since some components of the vectors are more sensitive than others the components should be individually weighted. This is implemented by taking pairs of faces, which might be of the same or different individuals and training a multi-layer perception, which forms the classifier, on the difference between the vectors to recognise these two classes enabling the classifier to decide whether or not the vectors are sufficiently similar to each other to be from the same face. If the answer is Y that is the classifier believes it is the same face then the wait until next check TFNC loop is followed and in due course the face of the user will again be checked to see that the same person is still at the workstation. In the event that a different person is detected at the workstation then the answer to SF? is N and further security measures are initiated IFSM (initiate further security measures). These could take various forms, for example audible or visible alarms, disabling the workstation, requiring the entry of a password, etc.

The sequence of operation of the security system for a computer workstation can be summarized as follows (neglecting the initial stage in which it grabs the image of the face of the user at logon).

1) Locate user face in image,
2) grab image of face,
3) extract face from background,
4) extract features from face,
5) compare current user face with logon user face,
6) if same user at 5) repeat 1) to 5) after given time interval, if different user at 5) initiate further security action.

The initial feature vector at logon is acquired using steps 1) to 4) above and the feature vector thus acquired is stored to enable the comparison step 5) to be carried out.

For other security applications modifications to this procedure may be required and corresponding system differences may occur. For example for access to a restricted area a person may have to stand in front of a camera in a defined position. Then either a search through a data base of faces of authorised persons is performed or by entering a code either by means of a card or a keyboard a comparison is made with the single stored face identified with that code.

For a credit card verification system a similar arrangement can be used in that a central data base of feature vectors of all authorized card users can be accessed by means of a transmission link from a transaction terminal. The terminal will include a video camera and means for extracting the face from the image produced by the camera and for generating the feature vector. This feature vector is then transmitted to the central data processing establishment where the feature vectors of all card holders are stored. The card number can be used to select the feature vector of the authorized user for the card from the store and the classifier used to determined whether the face captured by the transaction terminal is that of the authorized user. An authorisation or alarm signal as appropriate can then be transmitted to the transaction terminal to either give or withhold an authorisation for the card to be used.

An alternative arrangement is to have the feature vector of the authorized user stored on the card. In this case it is either necessary that the classifier is incorporated in the transaction terminal or that both the stored feature vector from the card and the feature vector generated by the transaction terminal are transmitted to a classifier at the central data processing establishment for the decision as to whether or not the person presenting the card is the authorised user to be made.

From reading the present disclosure, other modifications will be apparent to persons skilled in the art. Such modifications may involve other features which are already known in the design, manufacture and use of face classification and security systems and devices and component parts therefor and which may be used instead of or in addition to features already described herein.

What is claimed is:

1. A face classification system comprising:

input means for receiving video data representing a video image of a scene in which a face is present;

means for locating and extracting the video data representing the face in said scene;

transform means for processing the facial data to derive a feature vector representative of the face and which is rotation, scaling, translation and grey level intensity invariant; said transform means comprising means for fitting an outline to the face, means for locating the mid-point between the eyes, and means for producing a feature vector of the face by performing a Fourier-Mellin transformation on the facial data referenced to the mid-point between the eyes;

storage means for storing the feature vector; and comparing means for comparing the feature vector of the face in a present video image with a stored feature vector of a face in a previous video image to determine if the face in the present and previous video images is the same.

2. The face classification system as claimed in claim 1, wherein said transform means comprises a homomorphic filter.

3. The face classification system claimed in claim 1, wherein said transform means includes means for locating the eyes and nose of the face and means for sub-dividing the face by a first line joining the eyes and a second line perpendicular thereto and extending through the nose; and said recursive second order sub-division of moments includes a first sub-division of moments relative to said first line and a second sub-division of moments relative to said second line.

4. A security system comprising:

a video camera for producing video data representing a picture frame of a scene in which a face is present;

means for locating in the video data and extracting therefrom data representing the face in the picture frame;

transform means for processing the facial data to derive a feature vector representative of the face and which is rotation, scaling, translation and gray level intensity invariant; said transform means comprising means for fitting an outline to the face, means for locating the mid-point between the eyes, and means for producing a feature vector of the face by performing a Fourier-Mellin transformation on the facial data referenced to the mid-point between the eyes;

means for storing a corresponding feature vector derived by said transform means which is representative of a face in a previous picture frame;

means for comparing the feature vector of the face in a present picture frame with the stored feature vector of a face in a previous picture frame, to determine whether the face in both picture frames is the same; and means for initiating a security measure if the face is not the same in both picture frames.

5. A computer terminal security system for periodically validating continued access to said terminal by a user; comprising:

a video camera for producing video data representing periodic picture frames of a scene which includes the face of a user of the terminal;

means for locating in the video data of a present picture frame and extracting therefrom the data representing the user's face;

transform means for processing the facial data of the present picture frame to derive a feature vector which is representative of the face in such picture frame and is rotation, scaling, translation and grey level intensity invariant; said transform means comprising means for fitting an outline to the face, means for locating the mid-point between the eyes, and means for producing a feature vector of the face by performing a Fourier-Mellin transformation on the facial data referenced to the mid-point between the eyes;

means for storing the feature vectors relating to user faces in the periodic picture frames; and means for comparing the feature vector of the user's face in the present picture frame with the feature vector of the user's face in a previous picture frame to determine if the user's face is the same in both pictures frames.

* * * * *